(12) United States Patent
Pritchett

(10) Patent No.: US 10,307,267 B2
(45) Date of Patent: Jun. 4, 2019

(54) SYSTEM FOR IMPLANTING A PROSTHESIS

(71) Applicant: James W. Pritchett, Seattle, WA (US)

(72) Inventor: James W. Pritchett, Seattle, WA (US)

( * ) Notice: Subject to any disclaimer, the term of this patent is extended or adjusted under 35 U.S.C. 154(b) by 161 days.

(21) Appl. No.: 15/435,702

(22) Filed: Feb. 17, 2017

(65) Prior Publication Data

US 2018/0235774 A1   Aug. 23, 2018

(51) Int. Cl.
*A61F 2/46* (2006.01)
*A61F 2/34* (2006.01)

(52) U.S. Cl.
CPC .............. *A61F 2/4609* (2013.01); *A61F 2/34* (2013.01); *A61F 2002/4623* (2013.01); *A61F 2002/4625* (2013.01); *A61F 2002/4629* (2013.01)

(58) Field of Classification Search
CPC .................................................. A61F 2/4609
See application file for complete search history.

(56) References Cited

U.S. PATENT DOCUMENTS

| | | | |
|---|---|---|---|
| 5,320,625 A | 6/1994 | Bertin | |
| 5,431,657 A * | 7/1995 | Rohr | A61F 2/4609 606/91 |
| 5,584,837 A * | 12/1996 | Petersen | A61F 2/4609 606/86 R |
| 7,004,946 B2 | 2/2006 | Parker et al. | |
| 7,572,294 B2 * | 8/2009 | Meridew | A61F 2/34 623/22.12 |
| 7,931,656 B2 * | 4/2011 | Parry | A61F 2/4609 606/91 |
| 8,398,650 B1 * | 3/2013 | Burgi | A61F 2/4609 606/91 |
| 8,425,526 B2 | 4/2013 | Waltersdorff et al. | |
| 8,535,324 B2 * | 9/2013 | Aux Epaules | A61F 2/4609 606/100 |
| 9,119,731 B2 * | 9/2015 | Burgi | A61F 2/4609 |
| 2004/0177662 A1 * | 9/2004 | Bosse | A62B 3/005 70/465 |
| 2014/0114321 A1 | 4/2014 | Davenport et al. | |
| 2016/0100957 A1 | 4/2016 | Lewis | |
| 2016/0242934 A1 | 8/2016 | van der Walt et al. | |

OTHER PUBLICATIONS

Smith & Nephew R3 Acetabular System Surgical Technique by Smith & Nephew, copyright 2012, Smith & Nephew, Inc.
Zimmer Continuum Acetabular System Surgical Technique by Zimmer Biomedical, copyright 2015, Zimmer Inc.

* cited by examiner

*Primary Examiner* — Nicholas W Woodall
(74) *Attorney, Agent, or Firm* — Brooks Kushman P.C.

(57) ABSTRACT

A system for implanting an acetabular prosthesis includes a striker arrangement having a handle and a striker shaft with a distal end configured to engage an acetabular prosthesis. An elongate buttress shaft defines a longitudinal axis and is configured to receive the striker shaft therethrough; it is attachable to the striker shaft such that the distal end of the striker shaft extends beyond a distal face of the buttress shaft. The distal face has a larger diameter than a diameter of the distal end of the striker shaft and has a curved surface oriented transversely to the longitudinal axis.

16 Claims, 3 Drawing Sheets

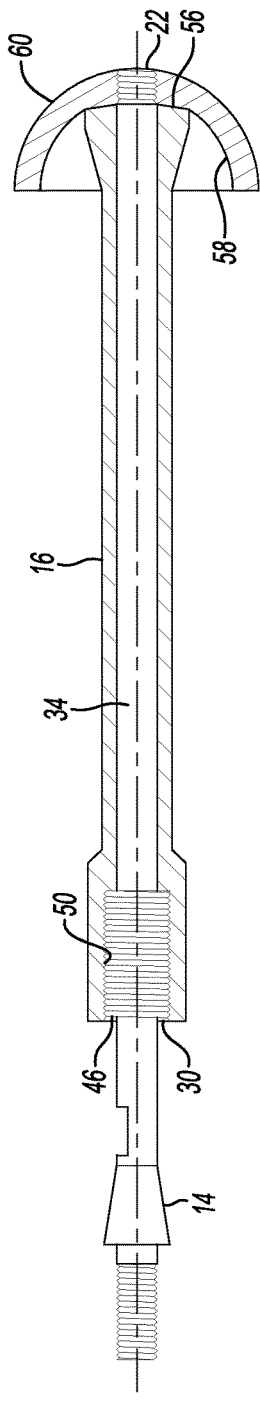
*Fig-3*
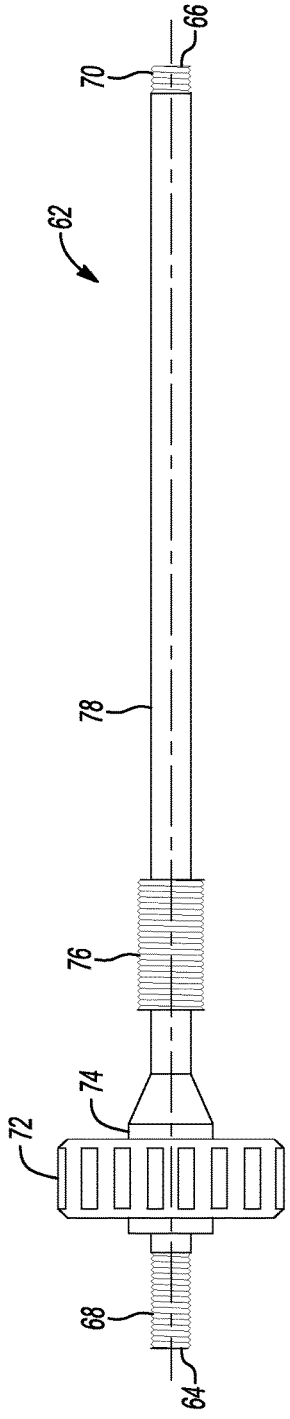
*Fig-4*
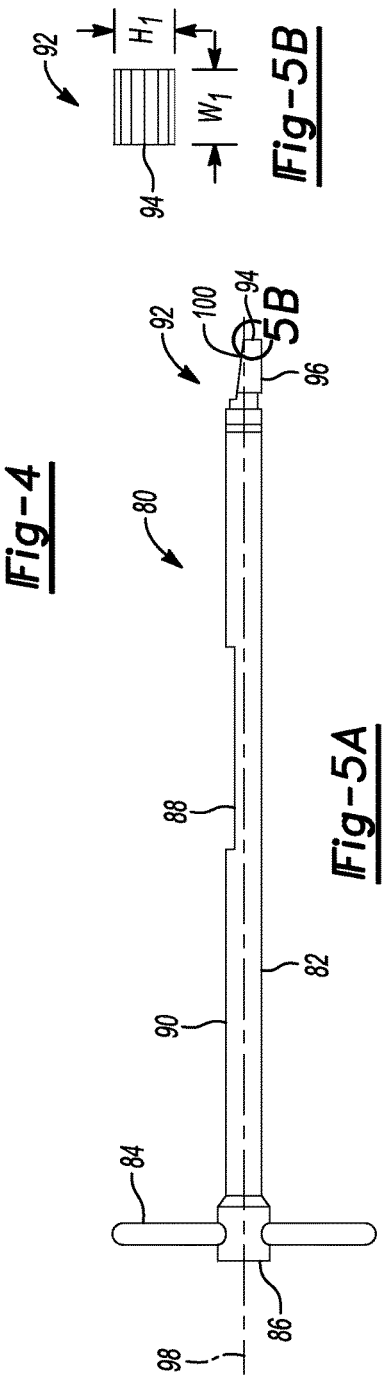
*Fig-5A*
*Fig-5B*

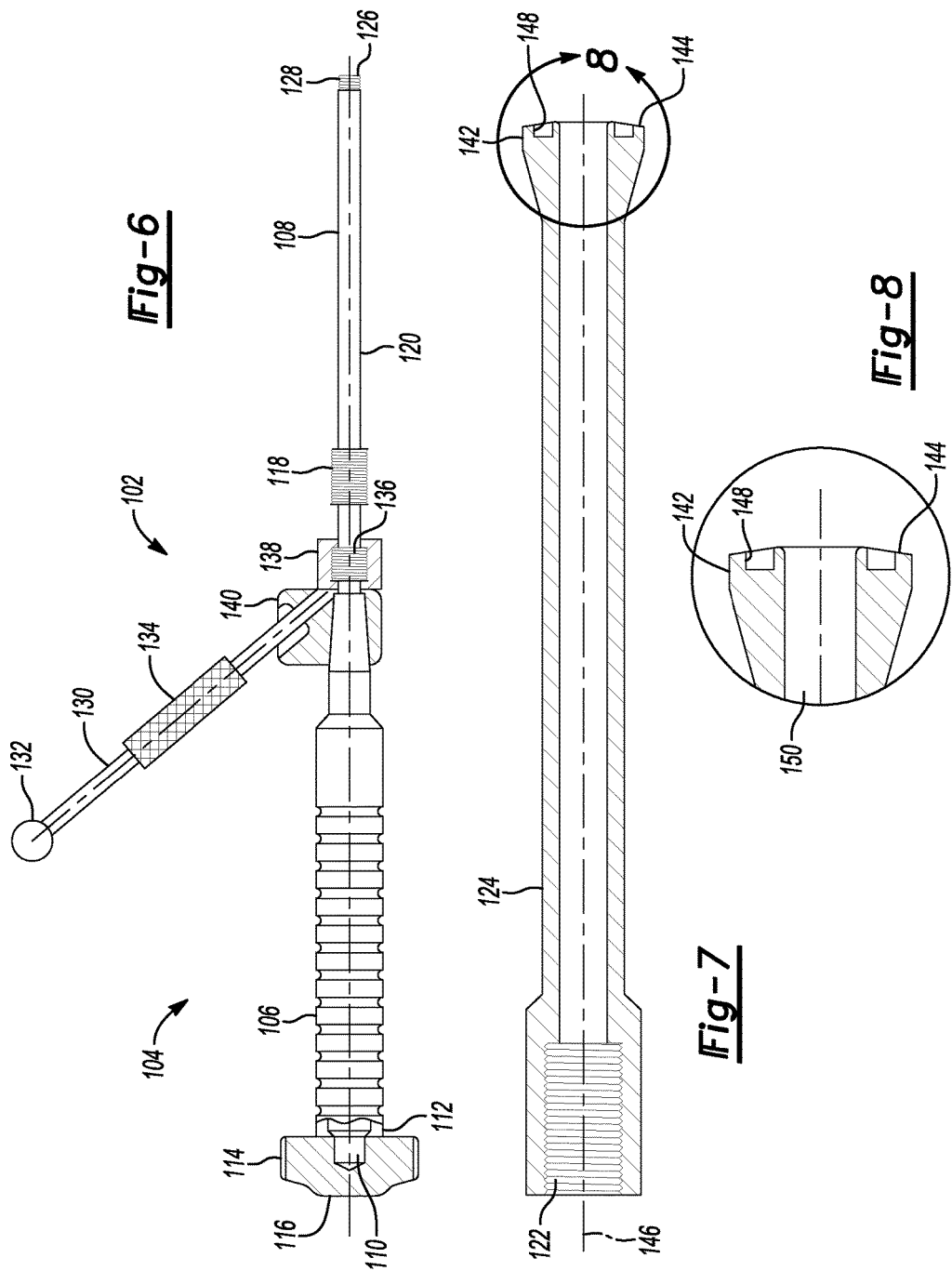

SYSTEM FOR IMPLANTING A PROSTHESIS

TECHNICAL FIELD

The present disclosure relates to a system for implanting an acetabular prosthesis.

BACKGROUND

Although hip replacement surgery has been common for several decades, and improvements continue to be made, there is still a desire to find ways to allow a patient to retain more of his or her own tissue, especially supporting bone structures. In a conventional total hip replacement, a metallic acetabular cup is affixed inside the patient's acetabulum, and a relatively thick polymeric insert is secured inside the acetabular cup. Because of the thickness of insert, the femoral side of the prosthesis includes a femoral head having a diameter that may be much smaller than the patient's own anatomy. Thus, bone is lost on the acetabular side when the acetabulum is reamed to accommodate the cup, and it is also lost on the femoral side when the neck and head of the patient's femur are resected to accommodate the stem and femoral head of the implant.

In contrast to a conventional total hip replacement, a hip resurfacing may be performed in certain cases, and this may allow a much greater retention of natural tissue. In at least some hip resurfacing surgeries, the head of the patient's femur is sculpted to accommodate a metal cap, and the acetabulum is reamed to accommodate a relatively thin, metal acetabular cup. The result is conservation of more bone than in a conventional total hip replacement, but the femoral side and acetabular side are both metal, which results in metal-to-metal contact and wear over the life of the implant.

Because the acetabular cup is relatively thin, enough bone must be reamed from the patient's acetabulum to ensure that the cup can be inserted with little impact force; otherwise, the thin cup is likely to deform as it is being positioned. Although it may be possible to make the acetabular cup thin enough to accept a polymeric insert, this adds to the likelihood of cup deformation—not only when it is inserted into the acetabulum, but when the insert is seated in the cup. Therefore, a need exists for a system for implanting an acetabular prosthesis that overcomes some or all of the aforementioned shortcomings of existing systems.

SUMMARY

At least some embodiments disclosed herein include a system for implanting an acetabular prosthesis. The system includes a handle and a solid striker shaft having a proximal end configured for attachment to the handle and a threaded distal end for securing the striker shaft to an acetabular prosthesis. The striker shaft also has an attachment feature. A hollow buttress shaft has an open proximal end, an open distal end, and a central channel extending along a longitudinal axis and between the open ends. The channel is sized and shaped to receive the striker shaft therein. The buttress shaft also includes an attachment feature that is configured to cooperate with the attachment feature of the striker shaft to secure the buttress shaft to the striker shaft.

The attachment feature of the buttress shaft is positioned such that the distal end of the striker shaft extends through the open distal end of the buttress shaft when the buttress shaft is secured to the striker shaft with the attachment features. The buttress shaft further includes an outside surface defined by a first diameter over a length of the buttress shaft, and the distal end of the buttress shaft has a second diameter larger than the first diameter. The distal end of the buttress shaft also includes a face oriented transversely to the longitudinal axis. The face has a curved surface positioned to contact an inside surface of an acetabular prosthesis when the buttress shaft is secured to the striker shaft with the attachment features and the acetabular prosthesis is secured to the distal end of the striker shaft.

At least some embodiments disclosed herein include a system for implanting an acetabular prosthesis. The system includes a striker arrangement including a handle and a striker shaft having a distal end configured to engage an acetabular prosthesis. An elongate buttress shaft defines a longitudinal axis and is configured to receive the striker shaft therethrough. The buttress shaft is attachable to the striker shaft such that the distal end of the striker shaft extends beyond a distal face of the buttress shaft. The distal face has a larger diameter than a diameter of the distal end of the striker shaft and further has a curved surface oriented transversely to the longitudinal axis.

At least some embodiments disclosed herein include a system for implanting an acetabular prosthesis that includes a striker arrangement. The striker arrangement includes a handle and a striker shaft having a distal end with threads configured to engage an acetabular prosthesis. A tubular buttress shaft is configured to be positioned over an outside surface of the striker shaft and secured to the striker shaft such that the threads extend beyond a distal end of the buttress shaft. The distal end of the buttress shaft includes a curved surface oriented transversely to a longitudinal axis of the buttress shaft.

BRIEF DESCRIPTION OF THE DRAWINGS

FIG. 3 shows a partial sectional view of a portion of the system shown in FIG. 1 with a striker shaft attached to an acetabular cup;

FIG. 4 shows a striker shaft in accordance with embodiments of a system described herein;

FIG. 5A shows a side view of an insert impactor as part of a system for implanting an acetabular prosthesis in accordance with embodiments described herein;

FIG. 5B shows a detail view of an end of the insert impactor show in FIG. 5A;

FIG. 6 shows a system in accordance with embodiments described herein, including an alignment handle;

FIG. 7 shows a buttress shaft for a system in accordance with embodiments described herein having an impact face accommodating an elastomeric ring; and FIG. 8 shows a close-up, detailed view of the impact face of the buttress shaft shown in FIG. 7.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
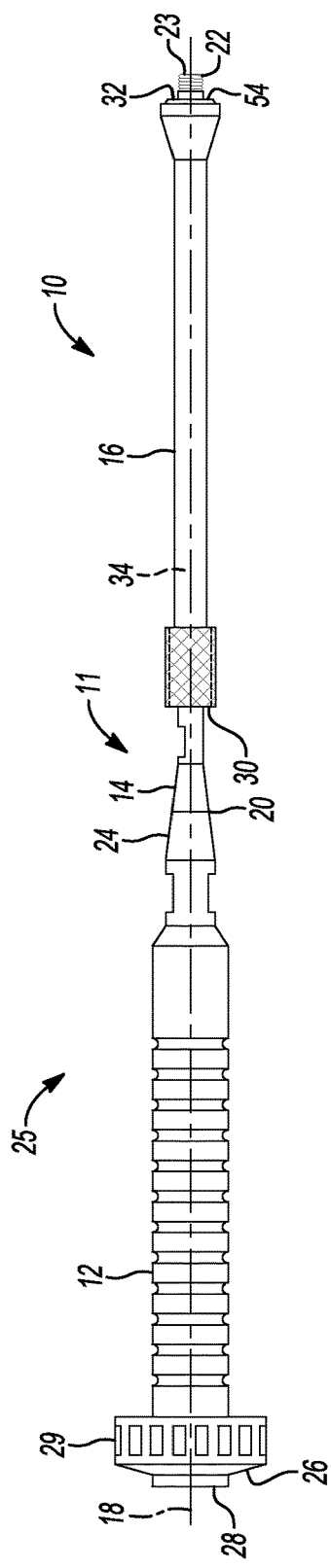
FIG. 1 shows a system for implanting an acetabular prosthesis in accordance with embodiments described herein.

FIG. 1 shows a system 10 for implanting an acetabular prosthesis in accordance with embodiments described herein. The system 10 includes a cup impactor 11, which has a handle 12, a striker shaft 14, and an elongate, hollow buttress shaft 16. The cup impactor 11 is shown in FIG. 1 as an assembled system. In this embodiment, the striker shaft 14 is a solid rod; however, in other embodiments a striker rod may be partly or even completely hollow. When assembled, the handle 12, the striker shaft 14, and the buttress shaft 16 share a common longitudinal axis 18. The striker shaft 14 has a proximal end 20 and a distal end 22, which includes male threads 23 configured to engage female threads on an acetabular cup, as explained in more detail below. The proximal end 20 is configured for attachment to a distal end 24 of the handle 12, and together the handle 12 and the striker shaft 14 may be conveniently referred to as a striker arrangement 25.

A proximal end 26 of the handle 12 is configured with an impact surface 28 configured to receive blows from a mallet during insertion of an acetabular cup. Disposed near the proximal end 26 of the handle 12 is a knob 29, which helps to keep a practitioner's hand properly located while the acetabular cup is impacted into the patient. In the embodiment illustrated in FIG. 1, the striker shaft 14, the buttress shaft 16, and the handle 12 are each made from a stainless steel material, although in other embodiments, different materials may be used. The knob 29 may be attached to the handle 12 by welding, pins, or any other attachment mechanism effective to achieve the required strength of attachment.

Figure 2:
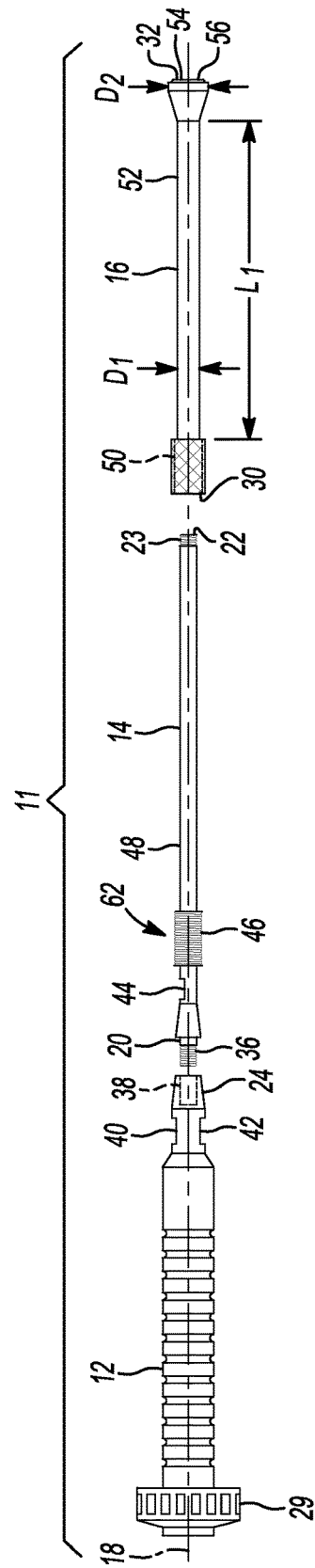
FIG. 2 shows an exploded view of the system shown in FIG. 1.

The buttress shaft 16 is tubular and includes an open proximal end 30 and an open distal end 32. As described above, the buttress shaft 16 is hollow, and includes a central channel 34 extending along the longitudinal axis 18 between the open ends 30, 32—see, also FIG. 3. The channel 34 is configured—e.g., sized and shaped—to receive the striker shaft 14 therein. FIG. 2 shows an exploded view of the cup impactor 11, and illustrates the threaded attachments between the handle 12 and the striker shaft 14, and between the striker shaft 14 and the buttress shaft 16. Specifically, male threads 36 at the proximal end 20 of the striker shaft 14 are configured to mate with female threads 38 inside the distal end 24 of the handle 12. In the embodiment illustrated in FIGS. 1 and 2, flat portions 40, 42 on the handle 12 and flat portion 44 on the striker shaft 14 are configured to accommodate pliers or other tools to allow the striker shaft 14 to be securely tightened to the handle 12. In other embodiments, a knob or other features may be employed to facilitate assembly of the handle 12 to the striker shaft 14—see, e.g., FIG. 4.

As shown in FIG. 2, the striker shaft 14 includes an attachment feature 46, which, in this embodiment, includes male threads disposed on an outside surface 48 of the striker shaft 14. The threads 46 are disposed toward the proximal end 20 of the striker shaft 14—i.e., the threads 46 are closer to the proximal end 20 than they are to the distal end 22. The buttress shaft 16 also includes an attachment feature 50, which, in this embodiment, includes female threads disposed inside the proximal end 30. Because the threads 23 on the end 22 of the striker shaft 14 are right-hand threads configured to engage the acetabular cup, it may be convenient to make the threads 46 on the striker shaft 14, and the threads 30 on the buttress shaft 16, left-hand threads so that they will remain secure while the threads 23 are engaged with the acetabular cup. As shown in FIG. 1, the distal end 22 of the striker shaft 14 extends through the open distal end 32 of the buttress shaft 16 when the cup impactor 11 is assembled—or more particularly, when the buttress shaft 16 is secured to the striker shaft 14 with the threaded attachment features 46, 50. Although the buttress shaft 16 is attached to the striker shaft 14 with a threaded engagement in this embodiment, other embodiments contemplate different ways of attaching a striker shaft to a buttress shaft—e.g., a quick-connect system as may be found in pneumatic hose connections.

Although it may be used with a conventional total hip replacement surgery, the system 10 may be particularly well-suited for use in hip resurfacing surgery where a very thin acetabular cup is used. For example, it may be possible to use a polymeric insert inside the acetabular cup in a hip resurfacing surgery if the acetabular cup is less than 3 millimeters (mm) thick. This may provide advantages over having a metal-to-metal arrangement, where a metal femoral surface articulates within the metal acetabular surface. In the case of a resurfacing acetabular cup that is configured to receive a polymeric insert, and is therefore very thin—e.g., having a thickness of approximately 2 mm—there are very few female threads to engage with the threads 23 on the striker shaft 14. If the male threads 23 on the striker shaft 14 were the only contact surface between the cup impactor 11 and the acetabular cup, it would be very easy for the threads on one or both of the striker shaft 14 and the acetabular cup to be stripped.

The system 10 addresses this issue by providing a cup impactor 11 with the buttress shaft 16 having a relatively large diameter at the distal end 32. More specifically, the buttress shaft 16 has an outside surface 52 defined by first diameter ($D_1$) along a length ($L_1$), and a second diameter ($D_2$) larger than the first diameter ($D_1$) at the distal end 32. In at least some embodiments, the first diameter ($D_1$) may be between 0.4 and 0.5 inches (in.), with a diameter of the channel 34 being between 0.3 and 0.4 in. The diameter of the channel 34 must be large enough to accommodate a relatively easy slide-fit for the striker shaft 14 to be inserted through it, and in some embodiments, an outside diameter of the portion of the striker shaft 14 going through the buttress shaft 16 may be between 0.25 and 0.35 in.

At the distal end 32 of the buttress shaft 16 is a distal face 54 oriented transversely to the longitudinal axis 18. The face 54 has a curved surface 56, which, as shown in FIG. 3, is positioned to contact an inside surface 58 of an acetabular cup 60 when the buttress shaft 16 is secured to the striker shaft 14 with the threaded attachment features 46, 50 and the acetabular cup 60 is secured to the distal end 22 of the striker shaft 14. More specifically, the external threads 46 on the striker shaft 14 are positioned at an attachment location 62 toward the proximal end 20 of the striker shaft 14 such that when the buttress shaft 16 is secured to the striker shaft 14, the threads 23 extend a small distance beyond the face 54. This allows the curved surface 56 of the face 54 to contact the inside surface 58 when the acetabular cup 60 is secured to the distal end 22 of the striker shaft 14. Because the distal face 54 of the buttress shaft 16 has a diameter that is larger than a diameter of the distal end 22 of the striker shaft 14—see FIG. 1—the force of impact is spread over a larger area on the inside surface 58 of the acetabular cup 60; this reduces stress and the likelihood of undesirable deformation of the cup 60 as it is inserted into the patient's acetabulum.

Because different patients require different sizes of acetabular cups, it may be convenient to have available a number of different buttress shafts, such as the buttress shaft 16, having different diameters—see, e.g., ($D_2$) in FIG. 2—toward their distal ends. It may also be convenient to have faces, such as the face 54, configured with surfaces having different curves to accommodate different sizes of acetabular cups. Even so, the radii of the internal, articulating surface of acetabular cups may not change so significantly over a range of cup sizes that it is necessary to have multiple buttress shafts. For example, the curved surface 56 on face 54 of the buttress shaft 16 may have a spherical radius of approximately 1.1 in., which may accommodate a full range of acetabular cup sizes. Other embodiments may include a buttress shaft having a distal face with a different spherical radius or with other curve configurations that may include multiple radii, and which may or may not be spherical.

FIG. 4 shows a striker shaft 62 forming a part of a system for implanting an acetabular prosthesis in accordance with embodiments described herein. The striker shaft 62 includes a proximal end 64 and a distal end 66, each of which includes male threads 68, 70, respectively. The threads 70 at the distal end 66 are configured to engage mating threads and an acetabular cup—see, e.g., FIG. 3. The threads and 68 at the proximal end 64 are configured to engage a handle, such as the handle 12 illustrated in FIGS. 1 and 2. In the embodiment shown in FIG. 4, the striker shaft 62 includes a knob 72 disposed toward the proximal end 64, and which extends radially outward therefrom. The knob 72 is sized and shaped to facilitate hand-tightening of the striker shaft 62 to a handle, such as the handle 12, and may provide a faster and more efficient attachment mechanism. The knob 72 may be attached to a base portion 74 of the striker shaft 62 by welding, pins, or any other way that is effective to achieve the required strength of attachment. The striker shaft 62 also includes threads 76 that are disposed on an outside surface 78, and which are configured to engage threads on a buttress shaft, such as the threads 50 on the buttress shaft 16 illustrated and described above.

In addition to an acetabular cup impactor, such as the cup impactor 11 illustrated and described above, systems in accordance with embodiments described herein may also include an insert impactor, such as the insert impactor 80 shown in FIGS. 5A and 5B. When a thin acetabular cup is used, for example, in a hip resurfacing surgery, it may not be practical or even practicable to use a polymeric insert, and so the prosthesis may provide metal articular surfaces on both the femoral side and the acetabular side. In some cases, however, it may be possible to use an insert even with a thin acetabular cup. As described above, an acetabular cup impactor, such as the cup impactor 11, may allow a very thin cup to be inserted into a patient without undesirable deformation. This may be true even if the acetabulum is conservatively reamed to retain more natural tissue, which typically makes it more difficult to seat the acetabular cup—i.e., more force is required to insert the cup when the acetabulum is "under-reamed", and this increases the likelihood that the cup will deform on insertion.

When a very thin acetabular cup—e.g., a cup that is 2 mm thick—is used, there may also be enough space to use a polymeric insert. In such a case, however, the insert may also be very thin, for example, on the order of 3-4 mm. This may also present a challenge for inserting it into the acetabular cup, because it and the cup are both very thin. Rather than using an impactor configured to contact the inside articulating surface of the insert, embodiments of systems described herein may use an insert impactor, such as the impactor 80 shown in FIGS. 5A and 5B. The impactor 80 includes a handle portion 82 having a T-bar 84 disposed at a proximal end 86, and a grip portion 88 disposed toward a center of the handle portion 82. In the embodiment illustrated in FIG. 5A, the grip portion 88 is configured as a cut-out; however, in other embodiments, it may be a knurled area or it may include an external grip disposed on an outside of a surface 90 of the handle portion 82. The handle portion 82 may be made from a stainless steel material, or any other material effective to allow the impactor 80 to be used to seat a polymeric insert in an acetabular cup.

The insert impactor 80 also includes an impactor tip 92, which may be made from a polymeric material, such as Delrin, or any other material effective to impact an edge of an insert such as described below. FIG. 5B shows a detail view of a portion of the tip 92, and in particular, shows that it has a generally rectangular, striated surface 94. The striations 94 may be molded into the polymeric material, or they may be cut or otherwise formed in a post-processing operation. In the embodiment illustrated in FIGS. 5A and 5B, the rectangular end of the tip 92 has a width ($W_1$) of approximately 10 mm and a height ($H_1$) of approximately 10 mm. This configuration allows the impactor tip 92 to fit firmly on an edge of a polyethylene acetabular insert, rather than sitting at the bottom of the articulating surface, as most insert impactors are configured to do. Although the end of the tip 92 is generally square in this embodiment, in other embodiments it may be rectangular—i.e., having different width and height dimensions—or it may be circular or have some other shape with non-orthogonal sides.

As illustrated in FIG. 5A, the impactor tip 92 includes a first side 96 that is generally parallel to a longitudinal axis 98 of the impactor 80. It also includes a second side 100 that is opposite the first side 96, and which is disposed at an angle to it. This configuration allows the impactor 80 to be tilted away from a line-of-sight of the surgeon, while still having one of the sides—in this case the second side 100—generally perpendicular to the edge of the insert. This, along with the striated surface 94, helps to ensure that the impactor tip 92 will not slip off of the edge of the insert while it is being seated.

FIG. 6 shows a system 102 for implanting an acetabular prosthesis in accordance with embodiments described herein. The system 102 includes an acetabular cup impactor 104, which, although similar to the cup impactor 11 described above, has some distinguishing features. The cup impactor 104 includes a handle 106 and a striker shaft 108. Rather than having a threaded attachment with the handle 106, the striker shaft 108 extends entirely through the handle 106 so that its proximal end 110 extends past a proximal end 112 of the handle 106. The proximal end 110 of the striker shaft 108 is then attached to a knob 114 having an impact surface 116 disposed thereon. The striker shaft 108 may be, for example, welded to the knob 114, which may both be made from a stainless steel material. In this embodiment, the handle 106 may be made from a polymeric material, for example, phenolic.

As shown in FIG. 6, the striker shaft 108 also includes threads 118 configured to mate with corresponding threads 122 on a buttress shaft 124—see FIG. 7. A distal end 126 of the striker shaft 108 includes threads 128 configured to mate with an acetabular cup such as described above. In this embodiment, however, the cup impactor 104 includes an alignment handle 130 attached to the striker shaft 108 at a non-parallel angle thereto. The alignment handle 130 may be made from a stainless steel material, for example, and may include a T-bar 132, which is shown in an end view in FIG. 6. The handle 130 may also include a grip portion 134, which also may be made from a stainless steel material, and which in the embodiment shown in FIG. 6 is configured to slide along the handle 130. The striker shaft 108 includes another set of threads 136 that are configured to receive a nut 138. A base 140 attaches to the striker shaft 108 through a tapered fit, and is held in place by the nut 138. The alignment handle 130 is attached to the base 140, and may be secured, for example, by welding, by pins, or by a threaded attachment, just to name a few. The alignment handle 130 may provide greater control for the surgeon as the acetabular cup is being inserted. In other embodiments, a similar construction may be achieved, for example, by merely curving or bending the striker shaft 108.

As described above, the cup impactor 104 also includes a buttress shaft 124, which is shown in FIG. 7. The buttress shaft 124 is configured similarly to the buttress shaft 16 described above. In particular, the buttress shaft 124 has a distal end 142 that is configured with a face 144 disposed to transversely to a longitudinal axis 146 of the buttress shaft 124. When the buttress shaft 124 is attached to the striker shaft 108 at the threaded attachments 118, 122, the threads 128 and the distal end 126 of the striker shaft 108 extend beyond the distal end 142 of the buttress shaft 124. In this way, the face 144—which in this embodiment is configured with a spherical radius—will contact an inside surface of an acetabular cup, such as described above and illustrated in FIG. 3. In the embodiment shown in FIG. 7, however, the distal face 144 of the buttress shaft 124 includes an annular groove 148. This is illustrated in detail in FIG. 8, which shows the groove 148 disposed around a central channel 150 of the hollow buttress shaft 124. The groove 148 is configured to receive an elastomeric ring, such as an O-ring, a D-ring, etc. This provides a more compliant material to contact the inside of the acetabular cup, which may be beneficial in some applications.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for implanting an acetabular prosthesis, comprising:
   a handle including a proximal end and a distal end;
   a solid striker shaft having a proximal end configured for threaded attachment to the distal end of the handle and a threaded distal end for securing the striker shaft to an acetabular prosthesis, the striker shaft including an attachment feature and further including a knob disposed toward the proximal end thereof and extending radially outward therefrom, the knob being sized and shaped to facilitate hand-tightening of the threaded attachment between the handle and the striker shaft; and
   a hollow buttress shaft having an open proximal end, an open distal end, and a central channel extending along a longitudinal axis and between the open ends, the channel being sized and shaped to receive the striker shaft therein, the buttress shaft including an attachment feature configured to cooperate with the attachment feature of the striker shaft to secure the buttress shaft to the striker shaft, the attachment feature of the buttress shaft being positioned such that the distal end of the striker shaft extends through the open distal end of the buttress shaft when the buttress shaft is secured to the striker shaft with the attachment features, the buttress shaft further including an outside surface defined by a first diameter over a length of the buttress shaft, and wherein the distal end of the buttress shaft has a second diameter larger than the first diameter and includes a face oriented transversely to the longitudinal axis, the face having a curved surface positioned to contact an inside surface of an acetabular prosthesis when the buttress shaft is secured to the striker shaft with the attachment features and the acetabular prosthesis is secured to the distal end of the striker shaft.

2. The system of claim 1, wherein the attachment feature of the striker shaft includes threads disposed on an outside surface and toward the proximal end thereof, and the attachment feature of the buttress shaft includes threads disposed inside the proximal end thereof.

3. The system of claim 1, wherein the curved surface of the face is defined by a spherical radius.

4. The system of claim 3, wherein the curved surface of the face includes an annular groove disposed therein configured to receive an elastomeric ring.

5. The system of claim 1, further comprising an insert impactor configured to seat an insert into an acetabular cup, the insert impactor including a handle and an impactor tip having a first side generally parallel to a longitudinal axis of the insert impactor and a second side opposite and disposed at an angle to the first side.

6. The system of claim 5, wherein the impactor tip includes a generally rectangular impactor surface having a plurality of striations thereon.

7. A system for implanting an acetabular prosthesis, comprising:
   a striker arrangement including a handle and a striker shaft having a distal end configured to engage an acetabular prosthesis;
   an elongate buttress shaft defining a longitudinal axis and configured to receive the striker shaft therethrough and attachable to the striker shaft such that the distal end of the striker shaft extends beyond a distal face of the buttress shaft, the distal face having a larger diameter than a diameter of the distal end of the striker shaft and having a curved surface oriented transversely to the longitudinal axis; and
   an insert impactor configured to impact an edge of an acetabular insert to seat the acetabular insert in an acetabular cup, the insert impactor including a handle and an impactor tip having a generally rectangular impactor surface with a plurality of striations thereon.

8. The system of claim 7, wherein the curved surface includes an annular groove disposed therein configured to receive an elastomeric ring.

9. The system of claim 7, wherein the striker shaft includes threads disposed on an outside surface toward a proximal end thereof, and the buttress shaft includes threads disposed inside the proximal end thereof configured to engage the threads on the outside surface of the striker shaft.

10. The system of claim 7, wherein the handle includes a proximal end and a distal end configured for threaded attachment to the proximal end of the striker shaft.

11. The system of claim 10, wherein the striker shaft includes a knob disposed toward the proximal end thereof and extending radially outward therefrom, the knob being sized and shaped to facilitate hand-tightening of the threaded attachment between the handle and the striker shaft.

12. The system of claim 7, wherein the buttress shaft is attachable to the striker shaft at an attachment location on the striker shaft that is disposed toward a proximal end thereof, and the curved surface is positioned to contact an inside surface of an acetabular prosthesis when the buttress shaft is attached to the striker shaft at the attachment location and the distal end of the striker shaft is engaged with the acetabular prosthesis.

13. A system for implanting an acetabular prosthesis, comprising:
   a striker arrangement including a handle and a striker shaft having a distal end with threads configured to engage an acetabular prosthesis;
   a tubular buttress shaft configured to be positioned over an outside surface of the striker shaft and secured to the striker shaft such that the threads extend beyond a distal end of the buttress shaft, the distal end of the buttress shaft including a curved surface oriented transversely to a longitudinal axis of the buttress shaft, the curved surface including an annular groove disposed therein configured to receive an elastomeric ring, the groove opening in a direction generally parallel to the longitudinal axis of the buttress shaft; and
   an insert impactor configured to impact an edge of an acetabular insert to seat the acetabular insert in an acetabular cup, the insert impactor including a handle and an impactor tip having a generally rectangular impactor surface with a plurality of striations thereon.

14. The system of claim 13, further comprising an alignment handle attached to the striker shaft at a non-parallel angle thereto.

15. The system of claim 13, wherein the buttress shaft is securable to the striker shaft at an attachment location on the striker shaft that is disposed toward a proximal end thereof, and the curved surface is positioned to contact an inside surface of an acetabular prosthesis when the buttress shaft is secured to the striker shaft at the attachment location and the threads at the distal end of the striker shaft are engaged with the acetabular prosthesis.

16. The system of claim 13, wherein the curved surface is defined by a spherical radius.

\* \* \* \* \*